United States Patent [19]

Manfuso, Jr.

[11] 4,083,991

[45] Apr. 11, 1978

[54] TOPICAL TREATMENT OF HERPES INFECTIONS WITH THIMEROSAL

[75] Inventor: John A. Manfuso, Jr., Chevy Chase, Md.

[73] Assignee: Burton, Parsons and Company, Inc., Washington, D.C.

[21] Appl. No.: 794,614

[22] Filed: May 6, 1977

[51] Int. Cl.² .................................. A61K 31/305
[52] U.S. Cl. ........................................... 424/291
[58] Field of Search ................................ 424/291

[56] References Cited

PUBLICATIONS

Baker et al., P.D.R., 27 Ed., 1973, pp. 895–896.

*Primary Examiner*—Jerome D. Goldberg
*Attorney, Agent, or Firm*—Fidelman, Wolffe & Waldron

[57] ABSTRACT

Herpes infections are treated topically with thimerosal (sodium ethylmercurithiosalicilate).

4 Claims, No Drawings

TOPICAL TREATMENT OF HERPES INFECTIONS WITH THIMEROSAL

BACKGROUND OF THE INVENTION

Thimerosal, (sodium ethylmercurithiosalylate, (Merck 8th Ed. pg. 1040)

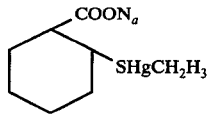

is a well known antiseptic for surface tissues employed in a dilute aqueous solution or in a tincture. In veterinary use it is employed as a wound antiseptic and in mycotic skin infections. It has been discovered that thimerosal has anti-viral properties. In vitro studies have shown that it is quite toxic to herpes simplex and in vivo studies with rabbits have shown it to be more effective than idouridine (IDU) (Merck, 8th Ed. pg. 561), a recognized anti-viral agent for herpes simplex keratitis. In addition, the thimerosal solution has no adverse effect on the epithelium where as IDU does exhibit such effects.

PREFERRED EMBODIMENT

Six albino rabbits were examined for any trace of bacterial or viral infections or other pathology present. Rabbit No. 2 had a slight bacterial infection in the right eye. The other eleven eyes were normal. Then all these eyes were corneal infected with Type I (Mckrae strain) herpes simplex virus. The rabbits were infected using 50 ul of viral suspension containing $10^7$ virus/ml. The animals received an antibiotic (chloramphenicol 0.5% solution) topically twice a day (in the morning and in the evening) to prevent successive bacterial infections. The treatment began on day 4 after inoculation. The 11 eyes were divided into 3 groups. 3 eyes received physiological isotonic saline solution, 4 eyes received 1:5000 uridine (IDU), and 4 eyes received thimerosal 1:5000 in aqueous solution, one drop each into each eye at every two hours between 9 AM and 9 PM, i.e. 7 times a day. The eyes were examined on day 4 prior to the beginning of the treatment, on day 6, on day 8, and on day 10, when the study was terminated. The rabbits were sacrificed, and epithelial swabs were cultured for the presence of live virus. On days 4, 6, 8 and 10 the animals were graded on a scale 1 to 4 for the condition of the corneal epithelium, the iris, and the conjunctive including the lid lining. The results are shown here:

| Animal # | Drug | EPITHELIUM (day postinfection) | | | |
|---|---|---|---|---|---|
| | | Day 4 | Day 6 | Day 8 | Day 10 |
| 1 OD | IDU | 0.50 | 0.50 | 0.37 | 0.87* (broke thru) |
| 4 OD | " | 0.37 | 0.05 | 0.25 | — |
| 5 OD | " | 0.75 | 0.50 | 0.50 | — |
| 6 OS | " | 0.37 | 0.37 | 0.37 | 0.05 |
| Ave. | | 0.50 | 0.36 | 0.37 | 0.23 |
| 3 OS | Thimerosal | 0.37 | 0.62 | 0.37 | 0.05 |
| 4 OS | " | 0.50 | 0.37 | 0.25 | — |
| 5 OS | " | 0.75 | 0.05(?) | 0.75 | 0.05 |
| 6 OD | " | 0.37 | 0.75 | 0.75 | 0.05 |
| Ave. | | 0.50 | 0.45 | 0.53 | 0.04 |
| 1 OS | Saline | 0.75 | 0.87 | 0.87 | 0.05 |
| 2 OS | " | 0.08 | 0.37 | 0.87 | 0.87 |
| 3 OD | " | 0.05 | 0.05 | 0.75 | 0.37 |
| Ave. | | 0.29 | 0.43 | 0.83 | 0.43 |
| IRITIS (day post-infection) | | | | | |
| 1 OD | IDU | — | — | 0.05 | 0.87 |
| 4 OD | " | — | — | 0.25 | 0.05 |
| 5 OD | " | 0.05 | — | 0.09 | 0.50 |
| 6 OS | " | — | — | — | — |
| Ave. | | 0.01 | 0.00 | 0.10 | 0.36 |
| 3 OS | $R_x$"X" | 0.05 | 0.25 | 0.05 | 0.25 |
| 4 OS | " | 0.05 | — | 0.075 | — |
| 5 OS | " | 0.05 | 0.075 | 0.37 | 0.37 |
| 6 OD | " | — | — | 0.25 | 0.37 |
| Ave. | | 0.04 | 0.08 | 0.186 | 0.25 |
| 1 OS | Saline | — | 1.00 | 0.25 | 0.25 |
| 2 OS | " | 0.870 | 0.75 | 0.50 | 1.00 |
| 3 OD | " | — | — | 0.05 | 0.75 |
| Ave. | | 0.29 | 0.58 | 0.27 | 0.67 |
| CONJUNCTIVITIS (days post-infection) | | | | | |
| 1 OD | IDU | — | — | 0.25 | 0.75 |
| 4 OD | " | 0.05 | — | 0.37 | 0.05 |
| 5 OD | " | 0.25 | 0.075 | 0.60 | 0.50 |
| 6 OS | " | — | 0.25 | 0.25 | 0.37 |
| Ave. | | 0.169 | 0.28 | 0.48 | 0.19 |
| 3 OS | $R_x$"X" | — | — | 0.25 | 0.75 |
| 4 OS | " | 0.25 | 0.37 | 0.05 | — |
| 5 OS | " | 0.375 | 0.25 | 0.87 | 0.50 |
| 6 OD | " | 0.05 | 0.50 | 0.75 | 0.25 |
| Ave. | | 0.169 | 0.28 | 0.48 | 0.19 |
| 1 OS | Saline | 0.075 | 1.00 | 0.50 | 0.50 |
| 2 OS | " | 0.870 | 0.75 | 0.87 | 1.00 |
| 3 OD | " | — | — | 0.05 | 0.50 |
| Ave. | | 0.315 | 0.58 | 0.62 | 0.67 |

The concentration of the thimerosal employed may range from 1:1000 to 1:5000 although a 1:5000 concentration will generally be found satisfactory. Although the rabbit test was conducted on infected corneas, other loci of herpes simplex infections may be treated with thimerosal solution with beneficial results.

In addition to being employed in an aqueous solution consisting solely of water and thimerosal. The latter may be incorporated in opthalmic solution containing other medicaments. For example, for the treatment of herpes simplex keratitis, thimerosal may be incorporated in the opthalmic aqueous solution disclosed in the patent to Rankin Pat. No. 3,767,788 containing polyethylene oxide and optionally, other ingredients.

Although the above comparative study is directed to rabbits it is well known that such tests are translatable to human use and similar results would be obtained upon human application. Therefore, the treatment of herpes simplex whether in human or animals is contemplated to be within the scope of this invention.

What is claimed:

1. A method for treating herpes simplex infection in a mammal comprising topically applying thimerosal to the infected area in an effective amount to treat herpes simplex infections.

2. The method of claim 1 wherein the thimerosal is applied in aqueous solution having concentration of 1:1000 to 1:5000.

3. The method of claim 2 wherein the thimerosal solution has a concentration of 1:5000.

4. The method of claim 3 wherein the thimerosal solution is applied to a cornea infected with herpes simplex.

* * * * *